United States Patent [19]

Reiser et al.

[11] Patent Number: 4,622,334
[45] Date of Patent: Nov. 11, 1986

[54] COMBATING FUNGI WITH 3-CYCLOALKYL-1-(1,3-DIOXAN-5-YL)2-(1,2,4-TRIAZOL-1-YL)-PROPAN-1-ONES AND PROPAN-1-OLS

[75] Inventors: Wolf Reiser; Wolfgang Krämer, both of Wuppertal; Karl H. Büchel, Burscheid; Wilhelm Brandes, Leichlingen; Paul Reinecke, Leverkusen, all of Fed. Rep. of Germany

[73] Assignee: Bayer Aktiengesellschaft, Leverkusen, Fed. Rep. of Germany

[21] Appl. No.: 637,451

[22] Filed: Aug. 3, 1984

[30] Foreign Application Priority Data

Aug. 11, 1983 [DE] Fed. Rep. of Germany ....... 3329128

[51] Int. Cl.$^4$ .................. A01N 43/653; A01N 55/02; C07D 405/06; C07F 3/00
[52] U.S. Cl. .................................... 514/383; 514/184; 548/101; 548/262; 549/372; 549/369; 570/186
[58] Field of Search ................ 548/101, 262; 514/184, 514/383

[56] References Cited

FOREIGN PATENT DOCUMENTS 0054865  6/1982  European Pat. Off. ............ 548/262
0062236 10/1982  European Pat. Off. ............ 548/262

Primary Examiner—Alton D. Rollins
Attorney, Agent, or Firm—Sprung Horn Kramer & Woods

[57] ABSTRACT

Combating fungi with a 3-cycloalkyl-1-(1,3-dioxan-5-yl)-2-(1,2,4-triazol-1-yl)-propan-1-one or -propan-1-ol of the formula

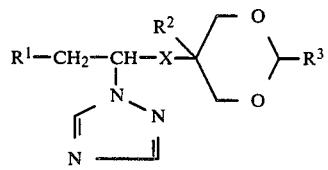

in which
$R^1$ is optionally substituted cycloalkyl,
$R^2$ is hydrogen or alkyl,
$R^3$ is hydrogen or alkyl and
X is

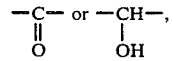

or a plant-tolerated addition product with an acid or metal salt.

8 Claims, No Drawings

COMBATING FUNGI WITH 3-CYCLOALKYL-1-(1,3-DIOXAN-5-YL)2-(1,2,4-TRIAZOL-1-YL)-PROPAN-1-ONES AND PROPAN-1-OLS

The invention relates to new 3-cycloalkyl-1-(1,3-dioxan-5-yl)-2-(1,2,4-triazol-1-yl)-propan-1-ones and -propan-1-ols, several processes for their preparation and their use as plant protection agents.

It has already been disclosed that certain cycloalkyl-triazolyl-alkanols, which are in each case vicinally substituted, such as, for example, 1-cyclohexyl-4,4-dimethyl-5-ethoxy-2-(1,2,4-triazol-1-yl)-pentan-3-ol, have fungicidal properties (compare DE-OS (German Published Specification) No. 3,048,267 and European Pat. No. 55,833).

It is furthermore known that 3-aryl-1-(1,3-dioxanyl)-2-triazolyl-propanones and -propanols, such as, for example, 3-(4-chlorophenyl)-1-(5-methyl-1,3-dioxan-5-yl)-2-(1,2,4-triazol-1-yl)-propan-1-ol, have fungicidal properties (compare DE-OS (German Published Specification) No. 3,113,628).

However, the action of these compounds is not always completely satisfactory, especially when low amounts and concentrations are used.

New 3-cycloalkyl-1-(1,3-dioxan-5-yl)-2-(1,2,4-triazol-1-yl)-propan-1-ones and -propan-1-ols of the general formula (I)

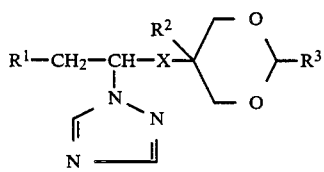

in which
$R^1$ represents optionally substituted cycloalkyl,
$R^2$ represents hydrogen or alkyl,
$R^3$ represents hydrogen or alkyl and
X represents the

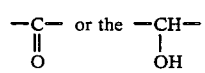

group,
and acid addition salts and metal salt complexes thereof which are tolerated by plants, have been found.

The compounds of the formula (I) can be obtained as diastereomeric and/or optical isomers or isomer mixtures of varying composition. Both the pure isomers and the isomer mixtures are claimed according to the invention.

It has furthermore been found that the new 3-cycloalkyl-1-(1,3-dioxan-5-yl)-2-(1,2,4-triazol-1-yl)-propan-1-ones and -propan-1-ols of the formula (I) are obtained by a process in which either (a) 3-cycloalkyl-1-(1,3-dioxan-5-yl)-2-halogeno-propan-1-ones of the general formula (II)

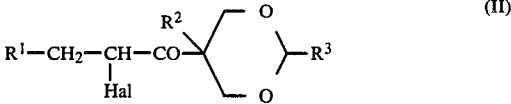

in which
$R^1$, $R^2$ and $R^3$ have the abovementioned meaning and Hal represents halogen,
are reacted with triazole, if appropriate in the presence of a diluent and if appropriate in the presence of an acid-binding agent, or (b) 1-(1,3-dioxan-5-yl)-2-(1,2,4-triazol-1-yl)-ethane-1-ones of the formula (III)

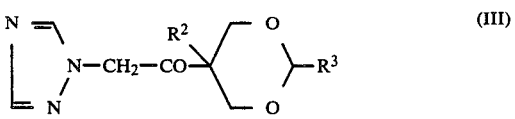

in which
$R^2$ and $R^3$ have the abovementioned meaning, are reacted with cycloalkyl-methyl halides of the formula (IV)

$$R^1-CH_2-Hal' \qquad (IV)$$

in which
$R^1$ has the abovementioned meaning and
Hal' represents halogen,
if appropriate in the presence of a diluent and if appropriate in the presence of an acid-binding agent, or (c) the 3-cycloalkyl-1-(1,3-dioxan-5-yl)-2-(1,2,4-triazol-1-yl)-propan-1-ones according to the invention, which are obtainable by process (a) or process (b), of the formula (Ia)

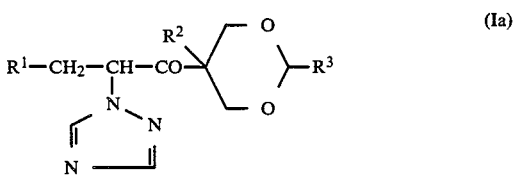

in which
$R^1$, $R^2$ and $R^3$ have the abovementioned meaning, are reduced by customary processes to give the 3-cycloalkyl-1-(1,3-dioxan-5-yl)-2-(1,2,4-triazol-1-yl)-propan-1-ols, according to the invention, of the formula (Ib)

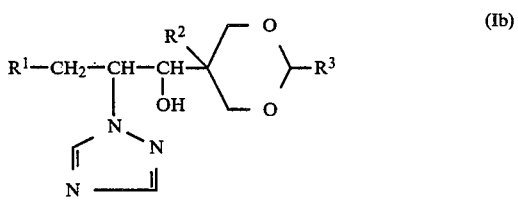

in which
$R^1$, $R^2$ and $R^3$ have the abovementioned meaning.

If appropriate, an acid or a metal salt can then be added onto the compounds of the general formula (I) thus obtained.

Finally, it has been found that the new 3-cycloalkyl-1-(1,3-dioxan-5-yl)-2-(1,2,4-triazol-1-yl)-propan-1-ones and -propan-1-ols of the general formula (I) have fungicidal properties.

Surprisingly, the 3-cycloalkyl-1-(1,3-dioxan-5-yl)-2-(1,2,4-triazol-1-yl)-propan-1-ones and -propan-1-ols according to the invention have a better fungicidal activity than the compounds 1-cyclohexyl-4,4-dimethyl-5-ethoxy-2-(1,2,4-triazol-1-yl)-pentan-3-ol and 3-(4-chlorophenyl)-1-(5-methyl-1,3-dioxan-5-yl)-2-(1,2,4-triazol-1-yl)-propan-1-ol, which are known from the prior art and are closely related compounds chemically and from the point of view of their action.

The substances of the formula (I) according to the invention thus represent a valuable enrichment of the prior art.

Formula (I) provides a general definition of the 3-cycloalkyl-1-(1,3-dioxan-5-yl)-2-(1,2,4-triazol-1-yl)-propan-1-ones and -propan-1-ols according to the invention. Preferred compounds of the formula (I) are those in which X represents the $$\underset{-C-}{\overset{O}{\|}} \quad \text{or the} \quad \underset{-CH-}{\overset{OH}{|}}$$

group, $R^1$ represents cycloalkyl which has 3 to 9 carbon atoms and is optionally monosubstituted or polysubstituted by identical or different straightchain or branched alkyl radicals with up to 4 carbon atoms and $R^2$ and $R^3$ independently of one another represent hydrogen or straight-chain or branched alkyl with up to 4 carbon atoms.

Particularly preferred compounds of the formula (I) are those in which

X represents the $$\underset{-C-}{\overset{O}{\|}} \quad \text{or the} \quad \underset{-CH-}{\overset{OH}{|}}$$

group, $R^1$ represents cyclopropyl, cyclopentyl, cyclohexyl or cycloheptyl, each of which is optionally mono-, di- or tri-substituted by identical or different methyl, ethyl, n- or i-propyl or n-, i-, s- or t-butyl radicals and $R^2$ and $R^3$ independently of one another represent hydrogen, methyl, ethyl, i-propyl or t-butyl.

The following compounds of the general formula (I) may be mentioned specifically, in addition to the compounds mentioned in the preparation examples:

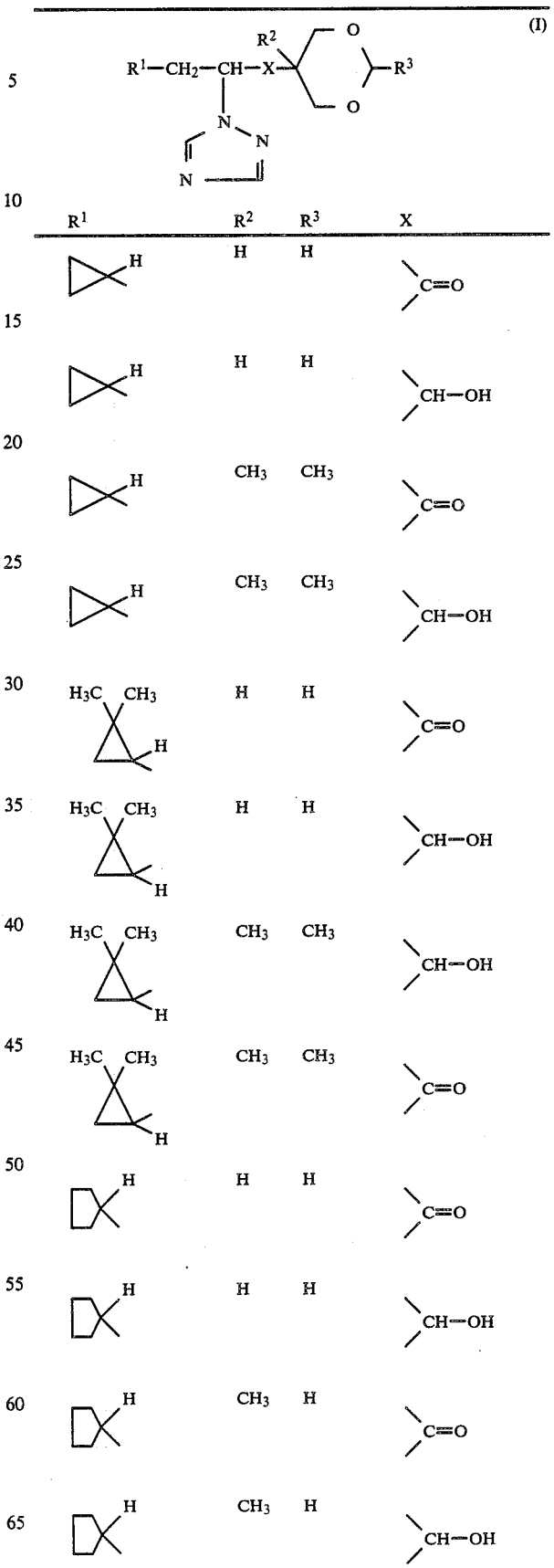

4,622,334

Table (continued) — Structure (I)

$$R^1-CH_2-CH(-N\text{-triazole})-X-C(R^2)(CH_2O)_2CH-R^3$$

Column 5

| R¹ | R² | R³ | X |
|---|---|---|---|
| cyclopentyl-H | H | CH₃ | C=O |
| cyclopentyl-H | H | CH₃ | CH—OH |
| cyclopentyl-H | CH₃ | CH₃ | C=O |
| cyclopentyl-H | CH₃ | CH₃ | CH—OH |
| CH₃-cyclopentyl-H | H | H | CH—OH |
| CH₃-cyclopentyl-H | H | H | C=O |
| CH₃-cyclopentyl-H | CH₃ | CH₃ | C=O |
| CH₃-cyclopentyl-H | CH₃ | CH₃ | CH—OH |
| cyclohexyl-H | CH₃ | CH₃ | C=O |
| cyclohexyl-H | CH₃ | CH₃ | CH—OH |
| cyclohexyl-H | H | H | C=O |
| cyclohexyl-H | H | H | CH—OH |
| cyclohexyl-H | H | CH₃ | C=O |

Column 6

| R¹ | R² | R³ | X |
|---|---|---|---|
| cyclohexyl-H | H | CH₃ | CH—OH |
| H₃C-cyclohexyl-H | H | H | C=O |
| H₃C-cyclohexyl-H | H | H | CH—OH |
| H₃C-cyclohexyl-H | CH₃ | CH₃ | C=O |
| H₃C-cyclohexyl-H | CH₃ | CH₃ | CH—OH |
| H₅C₂-cyclohexyl-H | CH₃ | CH₃ | C=O |
| H₅C₂-cyclohexyl-H | CH₃ | H | C=O |
| H₅C₂-cyclohexyl-H | H | CH₃ | CH—OH |
| H₅C₂-cyclohexyl-H | H | CH₃ | CH—OH |
| i-C₃H₇-cyclohexyl-H | CH₃ | CH₃ | C=O |
| i-C₃H₇-cyclohexyl-H | H | CH₃ | CH—OH |
| i-C₃H₇-cyclohexyl-H | CH₃ | H | C=O |

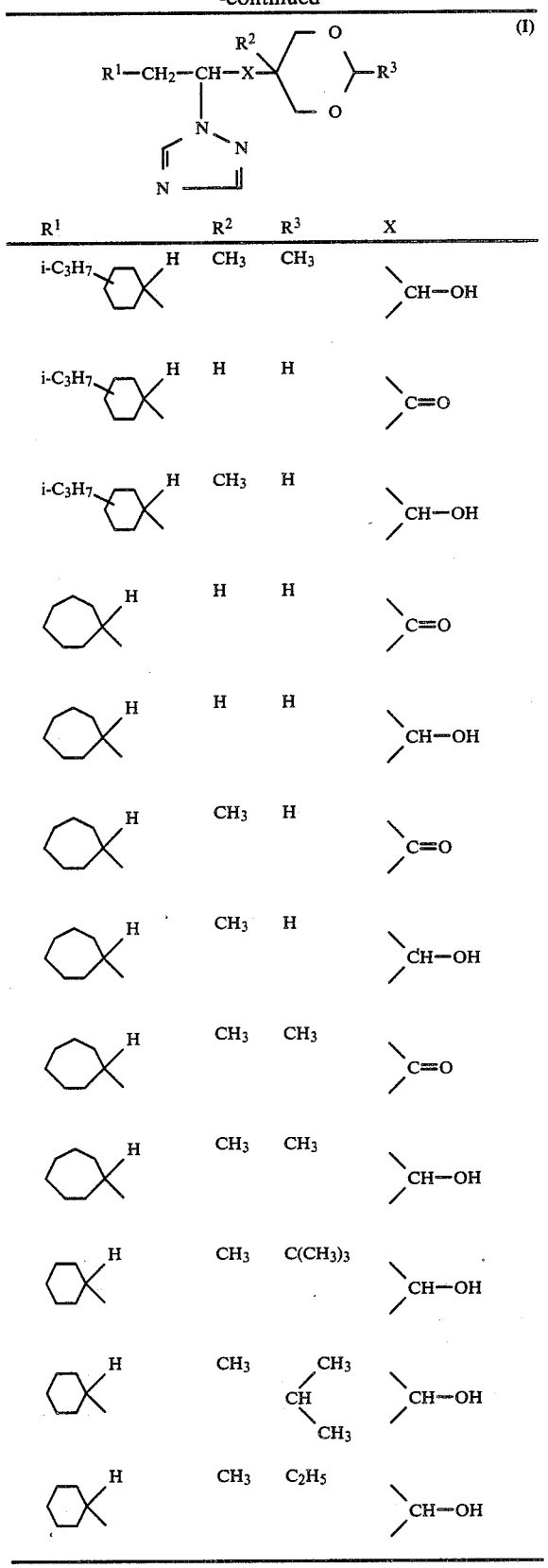

If, for example, 2-bromo-3-cyclohexyl-1-(1,3-dioxan-5-yl)-propan-1-one and triazole are used as starting substances, the course of the reaction in process (a) according to the invention can be represented by the following equation:

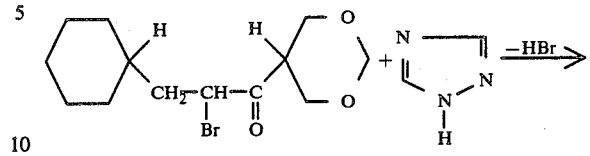

If, for example, 1-(5-methyl-1,3-dioxan-5-yl)-2-(1,2,4-triazole-1-yl)-ethane-1-one and cyclohexylmethyl bromide are used as starting substances, the course of the reaction in process (b) according to the invention can be represented by the following equation:

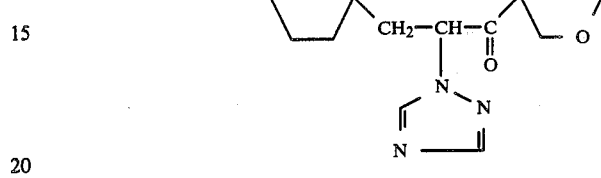

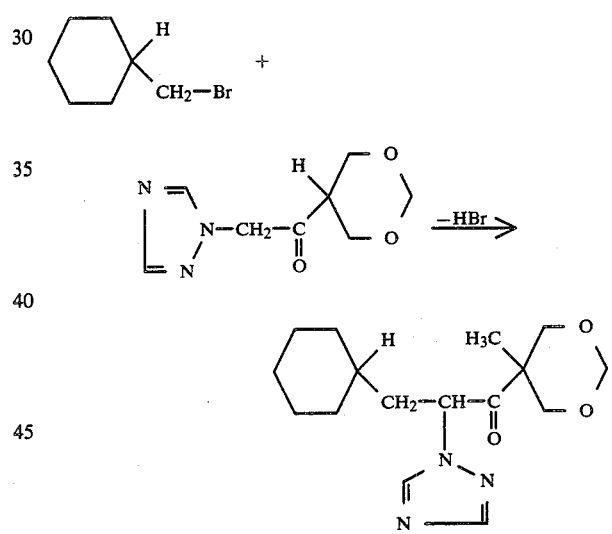

If, for example, 3-cyclohexyl-1-(2,5-dimethyl-1,3-dioxan-5-yl)-2-(1,2,4-triazol-1-yl)-propan-1-one is used as the starting substance and sodius borohydride is used as the reducing agent, the course of the reaction in process (c) according to the invention can be represented by the following equation:

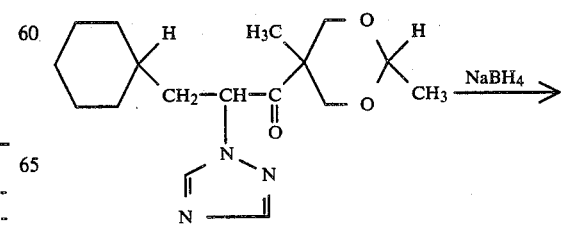

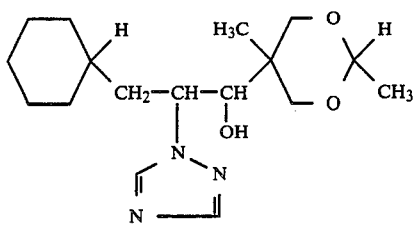

Formula (II) provides a general definition of the 3-cycloalkyl-1-(1,3-dioxan-5-yl)-2-halogenoketones required as starting substances for carrying out process (a) according to the invention. In this formula (II), $R^1$, $R^2$ and $R^3$ preferably have those meanings which have already been given as preferred for these radicals in the description of the substances of the formula (I) according to the invention. Hal preferably represents chlorine or bromine The 3-cycloalkyl-1-(1,3-dioxan-5-yl)-2-halogenoketones of the formula (II) are not yet known. However, they are obtained in a manner which is known in principle, by a process in which (1,3-dioxan-5-yl) methyl ketones of the formula (V)

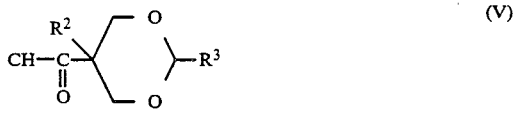

in which $R^2$ and $R^3$ have the abovementioned meaning, are first alkylated in a 1st stage by cycloalkylmethyl halides of the formula (IV)

$$R^1-CH_2-Hal' \quad (IV)$$

in which $R^1$ has the abovementioned meaning and

Hal' preferably represents chlorine or bromine, if appropriate in the presence of a diluent, such as, for example, dimethylformamide, and in the presence of a base, such as, for example, sodium hydride, at temperatures between 0° C. and 120° C. to give the 3-cycloalkyl-1-(1,3-dioxan-5-yl)-propan-1-ones of the formula (VI)

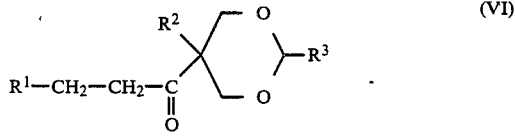

in which $R^1$, $R^2$ and $R^3$ have the abovementioned meaning, and these are halogenated in a 2nd stage with the aid of processes which are known in principle, for example with bromine in formamide (compare Chem. Ber. 93, 2083 [1960]) or with dioxane dibromide (compare Austr. J.Chem. 26, 1327 [1973]) or with the complex $Br_2$ x HBr x (pyrrolidone)$_3$ (compare Can.J.Chem. 47, 706 [1969]).

(1,3-Dioxan-5-yl) methyl ketones of the formula (V) are known (compare EP-OS (European Published Specification) No. 44,407 and DE-OS (German Published Specification) No. 3,113,628).

Formula (III) provides a general definition of the 1-(1,3-dioxan-5-yl)-2-(1,2,4-triazol-1-yl)-ethan-1-ones required as starting substances for carrying out process (b) according to the invention. In this formula (III), $R^2$ and $R^3$ preferably have those meanings which have already been given as preferred for these radicals in the description of the substances of the formula (I) according to the invention.

The 1-(1,3-dioxan-5-yl)-2-(1,2,4-triazol-1-yl)-ethan-1-ones of the formula (III) are likewise known (compare European Pat. No. 44,407 and DE-OS (German Published Specification) No. 3,113,628).

Formula (IV) provides a general definition of the cycloalkyl methyl halides also required for carrying out process (b) according to the invention and for the preparation of the starting substances of the formula (II). In this formula (IV), $R^1$ preferably has those meanings which have already been given as preferred for this radical in the description of the substances of the formula (I) according to the invention. Hal' preferably represents chlorine or bromine.

The cycloalkyl methyl halides are generally known compounds of organic chemistry.

Formula (Ia) provides a general definition of the 3-cycloalkyl-1-(1,3-dioxan-5-yl)-2-(1,2,4-triazol-1-yl)-1-propan-1-ones required as starting substances for carrying out process (c) according to the invention. The 3-cycloalkyl-1-(1,3-dioxan-5-yl)-2-(1,2,4-triazol-1-yl)-propan-1-ones of the formula (Ia) are compounds according to the invention and can be obtained by processes (a) and (b) according to the invention.

Possible diluents for process (a) according to the invention are inert organic solvents. These include, preferably, chlorinated hydrocarbons, such as, for example, methylene chloride, chloroform, carbon tetrachloride or chlorobenzene, amides, such as dimethylformamide, dimethyl cetamide or N-methylformanilide, nitriles, such as acetonitrile or propionitrile, and the highly polar solvents dimethylsulphoxide, sulpholane or hexamethylphosphoric acid triamide.

Process (a) according to the invention can be carried out in the presence of an acid-binding agent. It is possible to use all the inorganic or organic acid-binding agents which can customarily be used, such as alkali metal carbonates, for example sodium carbonate and potassium carbonate, or such as lower tertiary alkylamines, cycloalkylamines or aralkylamines, for example triethylamine, N,N-dimethylcyclohexylamine and N,N-dimethylbenzylamine. An appropriate excess of the triazole component is also possible.

The reaction temperatures can be varied within a substantial range in process (a) according to the invention. In general, the reaction is carried out between 0° C. and 150° C., preferably between 35° and 90° C.

For carrying out process (a) according to the invention, 1 to 3 mols of 1,2,4-triazole are preferably employed per mol of the compounds of the general formula (II). The compounds of the general formula (Ia) are isolated by customary methods.

Possible diluents for process (b) according to the invention are likewise inert organic solvents. These include, preferably, aromatic hydrocarbons, such as benzene, toluene or xylene, halogenated hydrocarbons, such as methylene chloride, chloroform, carbon tetrachloride or chlorobenzene, esters, such as ethyl acetate, amides, such as dimethylformamide, and dimethylsulphoxide.

Process (b) according to the invention is usually carried out in the presence of a base. All the customary organic and, in particular, inorganic bases can be used here, for example alkali metal hydroxides or alkali metal carbonates, such as sodium hydroxide, potassium hydroxide or potassium carbonate.

The reaction temperatures can be varied within a substantial range in carrying out process (b) according to the invention. In general, the reaction is carried out between 0° C. and 120° C., preferably between 20° C. and 100° C.

For carrying out process (b) according to the invention, equimolar amounts of cycloalkyl methyl halide of the formula (IV) and equimolar amounts of acid-binding agent are preferably employed per mol of the compounds of the general formula (III). The compounds of the general formula (Ia) are worked up and isolated by customary methods.

Process (c) according to the invention (reduction of the keto group) is carried out in the customary manner, such as, for example, by reaction of the compounds of the formula (Ia) with complex hydrides, if appropriate in the presence of a diluent; or by reaction with aluminum isopropylate in the presence of a diluent; or by reaction with hydrogen in the presence of a catalyst and if appropriate in the presence of a diluent.

If complex hydrides are used, possible diluents for the reduction reaction are polar organic solvents. These include, preferably, alcohols, such as methanol, ethanol, butanol and isopropanol, and ethers, such as diethyl ether or tetrahydrofuran. The reaction is in general carried out at 0° to 30° C., preferably at 0° to 20° C. For this reaction, about 1 mol of a complex hydride, such as sodium borohydride or lithium alanate, is employed per mol of the ketone of the formula (Ia). To isolate the reduced compounds of the formula (Ib), the residue is taken up in dilute hydrochloric acid and the mixture is then rendered alkaline and extracted with an organic solvent. Further working up is effected in the customary manner.

If aluminum isopropylate is used, possible diluents are the alcohols preferred for the abovementioned reduction, such as isopropanol, or inert hydrocarbons, such as benzene. The reaction temperatures can be varied within a substantial range; in general, the reaction is carried out between 20° and 120° C., preferably between 50° and 100° C. For carrying out the reaction, about 1 to 2 mols of aluminum isopropylate are employed per mol of the ketone of the formula (Ia). To isolate the reduced compounds of the formula (Ib), the excess solvent is removed by distillation in vacuo and the aluminum compound formed is decomposed with dilute sulphuric acid or sodium hydroxide solution. Further working up is effected in the customary manner.

If hydrogen is used, possible diluents for the reaction to be carried out are polar organic solvents. These include, preferably, alcohols, such as methanol and ethanol; and nitriles, such as acetonitrile. The reaction is carried out in the presence of a catalyst. Noble metal, noble metal oxide or noble metal hydroxide catalysts or so-called "Raney catalysts", in particular platinum, platinum oxide and nickel, are preferably used. The reaction temperatures can be varied within a substantial range. In general, the reaction is carried out between 20° and 50° C. The reaction can be carried out under normal pressure but also under increased pressure, for example under 1 to 2 atmospheres gauge. For carrying out the reaction, about 1 mol of hydrogen and 0.1 mol of catalyst are employed per mol of the compound of the formula (Ia). To isolate the reduced compounds of the formula (Ib), the catalyst is filtered off and the solvent is removed in vacuo. Further working up is effected in the customary manner.

The compounds of the formula (I) which can be prepared according to the invention can be converted into acid addition salts or metal salt complexes.

The following acids can preferably be used for the preparation of acid addition salts, which are tolerated by plants, of the compounds of the general formula (I): hydrogen halide acids, such as, for example, hydrochloric acid and hydrobromic acid, in particular hydrochloric acid, and furthermore phosphoric acid, nitric acid, sulphuric acid, monofunctional and bifunctional carboxylic acids and hydroxycarboxylic acids, such as, for example, acetic acid, maleic acid, succinic acid and fumaric acid, and sulphonic acids, such as, for example, p-toluenesulphonic acid and 1,5-naphthalenedisulphonic acid.

The acid addition salts of the compounds of the general formula (I) can be obtained in a simple manner by customary salt formation methods, for example by dissolving a compound of the general formula (I) in a suitable organic solvent and adding the acid, for example hydrochloric acid, and they can be isolated in a known manner, for example by filtration, and if appropriate purified by washing with an inert organic solvent.

Salts of metals of main groups II to IV and of subgroups I and II and IV to VIII can preferably be used for the preparation of metal salt complexes of the compounds of the general formula (I), examples of metals which may be mentioned being copper, zinc, manganese, magnesium, tin, iron and nickel.

Possible anions of the salts are those which, preferably, are derived from the following acids: hydrogen halide acids, such as, for example, hydrochloric acid and hydrobromic acid, and furthermore phosphoric acid, nitric acid and sulphuric acid.

The metal salt complexes of the compounds of the general formula (I) can be obtained in a simple manner by customary processes, thus, for example, by dissolving the metal salt in alcohol, such as, for example ethanol, and adding the solution to the compound of the general formula (I). The metal salt complexes can be isolated in a known manner, for example by filtration, and if appropriate purified by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating cereal diseases, such as, for example, against the leaf spot disease of barley causative organism (*Pyrenophora teres*), fruit diseases, such as, for example, against the powdery mildew of apple causative organism (*Podosphaera leucotricha*), or vegetable diseases, such as, for example, against the powdery mildew of cucumber causative organism (*Sphaerotheca fuliginea*).

In addition, the active compounds according to the invention also have an activity against species of powdery mildew of cereals and against rice disease causative organisms, such as, for example, *Pyricularia oyrzae*.

The active compounds can be converted to the customary formulations, such as solutions, emulsions, wettable powders, suspensions, powders, dusting agents, foams, pastes, soluble powders, granules, aerosols, suspension-emulsion concentrates, seed treatment powders, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs and azo- and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES:

EXAMPLE 1

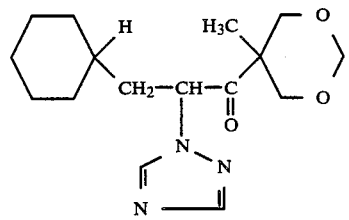

(Process b)

2.96 g (0.05 mol) of powdered potassium hydroxide and 3 ml of water are added to a solution of 11.0 g (0.05 mol) of 1-(5-methyl-1,3-dioxan-5-yl)-2-(1,2,4-triazol-1-yl)-ethan-1-one in 40 ml of dimethylsulphoxide, with stirring. After 10 minutes, 9.6 g (0.05 mol) of bromomethylcyclohexane (90% pure) are added and the mixture is stirred at 50° C. for 6 hours. For working up, the cooled reaction mixture is poured onto 500 ml of water and extracted twice with 200 ml of diethyl ether each time, the combined ether extracts are washed twice with 100 ml of water each time and dried over sodium sulphate and the solvent is removed in vacuo. The oily residue crystallizes from methylene chloride/diethyl ether. 8.0 g (52.1 g of theory) of 3-cyclohexyl-1-(5-methyl-1,3-dioxan-5-yl)-2-(1,2,4-triazol-1-yl)-propan-1-one of melting point 68°–71° C. are obtained.

EXAMPLE 2

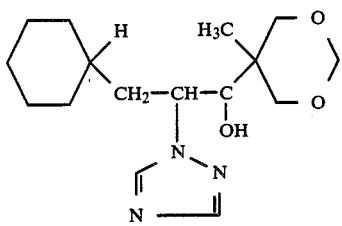

(Process c)

A solution of 0.7 g (0.02 mol) of sodium borohydride in 3 ml of 0.1 normal aqueous sodium hydroxide solution is added to a mixture of 6.0 g (0.02 mol) of 3-cyclohexyl-1-(5-methyl-1,3-dioxan-5-yl)-2-(1,2,4-triazol-1-yl)-propan-1-one, 2.3 g of powdered calcium chloride and 30 ml of ethanol, while cooling with ice. When the evolution of gas has ended, the precipitate formed is dissolved again by addition of 30 ml of ethanol and 50 ml of dilute hydrochloric acid, the solution is concentrated to 60 ml in vacuo and the concentrate is neutralized with aqueous bicarbonate solution and extracted twice with 100 ml of methylene chloride each time. The combined organic phases are washed with water, dried over sodium sulphate and freed from the solvent in vacuo. 6.3 g (100% of theory) of 3-cyclohexyl-1-(5-methyl-1,3-dioxan-5-yl)-2-(1,2,4-triazol-1-yl)-propan-1-ol are obtained as a colorless oil.

IR (cm$^{-1}$): 3667, 2999, 2853, 2772, 1670, 1612, 1510, 1480, 1450, 1384, 1307, 1277, 1236, 1164, 1139, 1087, 1070, 1029, 990, 932, 922, 888, 854, 725 and 675.

Use Examples

The compounds below are used as comparison substances in the use examples which follow:

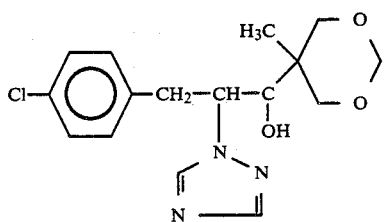

3-(4-Chlorophenyl)-1-(5-methyl-1,3-dioxan-5-yl)-2-(1,2,4-triazol-1-yl)-propan-1-ol

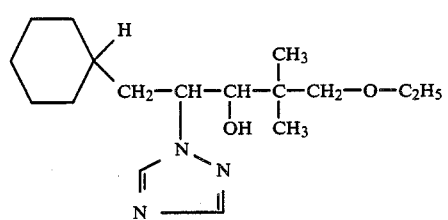

1-Cyclohexyl-4,4-dimethyl-5-ethoxy-2-(1,2,4-triazol-1-yl)-pentan-3-ol

Example A

Sphaerotheca test (cucumber)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus *Sphaerotheca fuliginea.*

The plants are then placed in a greenhouse at 23° to 24° C. and at a relative atmospheric humidity of about 75%.

Evaluation is carried out 10 days after the inoculation.

In this test, a clearly superior activity compared with the prior art is shown, for example, by the compound according to the following preparation example: 2.

Example B

Podosphaera test (apple)/protective/

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated by dusting with conidia of the powdery mildew of apple causative organism (*Podosphaera leucotricha*).

The plants are then placed in a greenhouse at 23° C. and a relative atmospheric humidity of about 70%.

Evaluation is carried out 9 days after the inoculation.

In this test, a clearly superior activity compared with the prior art is shown, for example, by the compound according to the following preparation example: 2.

Example C

*Pyrenophora teres* test (barley)/protective/

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Pyrenophora teres.* The plants then remain in an incubation cabinet at 20° C. and 100% relative atmospheric humidity for 48 hours.

The plants are placed in a greenhouse at a temperature of about 20° C. and a relative atmospheric humidity of about 80°.

Evaluation is carried out 7 days after the inoculation.

In this test, a clearly superior activity compared with the prior art is shown, for example, by the compounds according to the following preparation example: 2.

It will be understood that the specification and examples are illustrative but not limitative of the present invention and that other embodiments within the spirit and scope of the invention will suggest themselves to those skilled in the art.

We claim:

1. A 3-cycloalkyl-1-(1,3-dioxan-5-yl)-2-(1,2,4-triazol-1-yl)-propan-1-one or -propan-1-ol of the formula

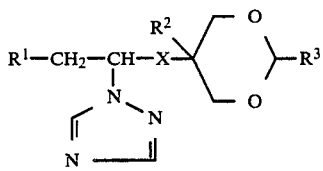

in which
R¹ is cycloalkyl which has 3 to 9 carbon atoms and is optionally substituted by alkyl with up to 4 carbon atoms, and
R² and R³ each independently is hydrogen or alkyl with up to 4 carbon atoms and
X is

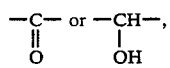

or a plant-tolerated addition product with an acid or metal salt.

2. A compound or addition product according to claim 1, in which
R¹ is cyclopropyl, cyclopentyl, cyclohexyl or cycloheptyl, each of which is optionally mono-, di- or tri-substituted by methyl, ethyl, n-propyl, i-propyl, n-butyl, i-butyl, s-butyl and/or t-butyl, and
R² and R³ each independently is hydrogen, methyl, ethyl, i-propyl or t-butyl.

3. A compound according to claim 1, wherein such compound is 3-cyclohexyl-1-(5-methyl-1,3-dioxan-5-yl)-2-(1,2,4-triazol-1-yl)-propan-1-one of the formula

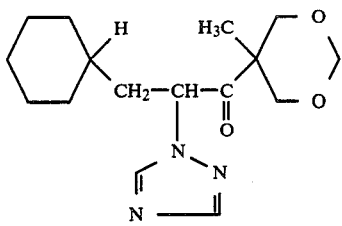

or a plant-tolerated addition product with an acid or metal salt.

4. A compound according to claim 1, wherein such compound is 3-cyclohexyl-1-(5-methyl-1,3-dioxan-5-yl)-2-(1,2,4-triazol-1-yl)-propan-1-ol of the formula

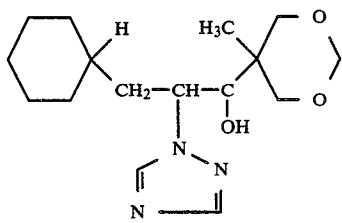

or a plant-tolerated addition product with an acid or metal salt.

5. A fungicidal composition comprising a fungicidally effective amount of a compound or addition product according to claim 1 in admixture with a diluent.

6. A method of combating fungi which comprises applying to such fungi or to a fungus habitat a fungicidally effective amount of a compound or addition product according to claim 1.

7. A method of combating fungi which comprises applying to such fungi or to a fungus habitat a fungicidally effective amount of a compound or addition product according to claim 3.

8. A method of combating fungi which comprises applying to such fungi or to a fungus habitat a fungicidally effective amount of a compound or addition product according to claim 4.

* * * * *